United States Patent [19]
Sherman

[11] Patent Number: 5,879,714
[45] Date of Patent: Mar. 9, 1999

[54] CONTROLLED-RELEASE PHARMACEUTICAL COMPOSITIONS

[75] Inventor: Bernard Charles Sherman, Willowdale, Canada

[73] Assignee: Bernard Charles Sherman, Ontario, Canada

[21] Appl. No.: 839,022

[22] Filed: Apr. 23, 1997

[30] Foreign Application Priority Data

Apr. 24, 1996 [NZ] New Zealand .............................. 286451

[51] Int. Cl.⁶ ....................................................... A61K 9/14
[52] U.S. Cl. ........................... 424/489; 424/464; 424/469; 424/470; 424/451; 424/457
[58] Field of Search ..................... 424/489, 464, 424/469, 470, 451, 457

[56] References Cited

U.S. PATENT DOCUMENTS

| 2,809,916 | 10/1957 | Hermelin | 424/500 |
| 3,068,143 | 11/1962 | Christenson et al. | 514/549 |
| 4,369,112 | 1/1983 | Vincent | 210/321.84 |
| 4,412,986 | 11/1983 | Kawata et al. | 514/356 |
| 4,673,564 | 6/1987 | Kawata et al. | 514/781 |
| 4,765,989 | 8/1988 | Wong | 424/473 |
| 5,047,244 | 9/1991 | Sanvordeker | 424/435 |
| 5,286,497 | 2/1994 | Hendrickson | 424/490 |

FOREIGN PATENT DOCUMENTS

| 1137379 | 12/1968 | European Pat. Off. . |
| 0557244A1 | 8/1993 | European Pat. Off. . |
| 1021924 | 3/1996 | European Pat. Off. . |
| 270439 | 2/1996 | New Zealand . |
| 270439 | 4/1996 | New Zealand . |
| 1021924 | 3/1966 | United Kingdom . |
| 1137379 | 12/1968 | United Kingdom . |
| 1456618 | 11/1976 | United Kingdom . |

*Primary Examiner*—D. Gabrielle Brouillette
*Attorney, Agent, or Firm*—Nixon & Vanderhye PC

[57] ABSTRACT

A controlled-release pharmaceutical composition for oral administration comprising a multitude of granules made by dissolving or dispersing a drug and a water-insoluble polymer in a molten carrier, solidifying the resultant material, and grinding the resultant solid into granules.

10 Claims, No Drawings

CONTROLLED-RELEASE PHARMACEUTICAL COMPOSITIONS

FIELD OF INVENTION

The present invention relates to controlled-release pharmaceutical compositions for oral administration.

BACKGROUND

The use of controlled-release compositions (also known as slow-release, sustained-release, or extended-release) is well established in medicine. Controlled-release formulations have the advantage that the active drug is gradually released over a relatively long period so that the drug is maintained in the blood stream for a longer time and at a more uniform concentration than would otherwise be the case. This allows administration only once or ice daily for drugs that would otherwise have to be taken more frequently to maintain required blood levels.

Many different types of controlled-release oral dosage forms have been developed, but each has disadvantages which affect its suitability to a particular drug and therapeutic objective.

The prior art discloses many compositions which incorporate the drug into a water-insoluble matrix, from which the drug will be slowly released in gastrointestinal fluid.

In the process of British Patent No. 1021924, the drug is admixed with a sustained-release material to obtain a mixture which is subsequently pressed into tablets. The sustained release material is used in amounts of as much as 95%, which results in substantial cost for this material and also produces a tablet larger than otherwise required.

British Patent No. 1137379 discloses use of ethylcellulose as a water-insoluble binder. The ethylcellulose is dissolved in alcohol and the solution is mixed with the drug in a multistep process. The alcohol must be evaporated, and the process is complex and not economical.

U.S. Pat. No. 2809916 also discloses a formulation process using repeated steps of mixing a drug with a water-insoluble excipient, drying and granulating.

In other prior art compositions the drug is incorporated into a matrix that is water-soluble but dissolves away only slowly to release the drug. The use of hydrophilic polymers such as hydroxypropylmethylcellulose as sustained-release matrix materials is well-known.

For example, U.S. Pat. Nos. 3065143 and 4369112 disclose the use of hydrophilic gums, including hydroxypropylmethylcellulose, as carrier base materials in the preparation of sustained-release pharmaceutical tablets.

As aforesaid, controlled-release tablets can be made by incorporating the drug into a matrix that is either water-insoluble or slowly water-soluble. However, in either case there are difficulties in achieving a uniform rate of release.

If the matrix is water-insoluble, the drug tends to be initially released relatively rapidly as the drug near the surface leaches out, and the rate of drug release then gradually reduces.

If the matrix is water-soluble, the layer at the surface gradually dissolves to expose more drug, so that the rate of release is more uniform over time than with a water-insoluble matrix. However, compositions of this type tend to suffer from "food effect". That is to say, release rate tends to be higher when the tablet is taken with food then without. This is because, with food, the gastrointestinal motility is higher and the increased agitation causes the tablet to dissolve away more rapidly.

It is possible to obtain rates of release that are more consistent using a "multi-granular" composition, by which is meant a composition that is comprised of and disintegrates in gastrointestinal fluid into a multitude of smaller individual granules, pellets, beads or tablets, each of which is itself a controlled-release composition.

For example, U.S. Pat. No. 5286497 discloses controlled-release compositions of diltiazem hydrochloride which are comprised of a multitude of beads which are contained with a gelatin capsule. However, such compositions are difficult and expensive to produce.

Drugs with low solubility in water (by which is meant having a solubility of less than 0.1 percent by weight in water at 20° C.) cause additional formulation problems due to their poor rate and extent of dissolution in aqueous media (including gastrointestinal fluids), which results in low absorption into systemic circulation after oral ingestion.

Examples of drugs with low solubility in water are some substituted dihydropyridine compounds, such as nifedipine, felodipine, nimodipine, isradipine, nitrendipine, nicardipine, niludipine, nisoldipine, and amlodipine. These compounds are classified as calcium antagonists, which are widely used for the treatment of cardiovascular disorders such as hypertension.

In order to make a controlled-release composition containing such a drug that will enable maximum absorption from the gastrointestinal tract, in addition to incorporating a feature to control the rate of release, it is necessary to incorporate in the composition a second feature that increases the solubility of the drug to enable it to dissolve in the gastrointestinal fluids.

Several ways to increase the solubility have been described in prior literature. One way is described in U.S. Pat. No. 4673564, wherein nicardipine is used in its amorphous form in order to obtain increased dissolution and absorption. U.K. I 456618 discloses improving the dissolution and absorption of nifedipine by preparation of a solid solution of nifedipine in polyethylene glycol in the presence of a surface active agent.

U.S. Pat. No. 4412986 discloses improving the dissolution and absorption of nifedipine by preparing a co-precipitate with a water-soluble polymer.

As aforesaid, in order to produce a controlled-release composition of a drug having low solubility in water, it is necessary to have one feature to increase the solubility and a second feature to slow down and control the rate of dissolution.

The prior art also discloses numerous compositions which include a feature of each type to achieve controlled-release of a drug having low solubility in water.

European patent application 0557-244-Al discloses compositions which contain nifedipine which has been micronized to small crystals to increase solubility, along with a hydrophilic gel-forming polymer to slow-down and control the rate of dissolution and absorption. A problem with the compositions disclosed in this patent is that the smallest size to which nifedipine can be micronized using conventional equipment is about 1 micron, and this particle size is still not small enough to enable full dissolution and absorption of the nifedipine. Moreover, unless the crystal size is carefully controlled-to be the same in every batch of tablets, release characteristics may vary from batch to batch. Another problem is that, as aforesaid, the use of a hydrophilic polymer as the agent to control rate of release causes the composition to be subject to a "food effect".

New Zealand patent application No. 270439 discloses a controlled-release tablet in which nifedipine is dissolved in a molten polyethylene glycol and which further incorporates a hydrophilic polymer. Again, the use of a hydrophilic polymer causes the composition to be subject to a "food effect".

U.S. Pat. No. 4765989 discloses a controlled-release formulation of nifedipine in the form of an osmotic device, which gives a reliable and uniform rate of release, but is relatively difficult and expensive to manufacture.

In view of the difficulties as aforesaid with prior art compositions, it is an object of the invention to enable production of a controlled-release composition which can be easily made, without the use of solvents that require evaporation in the process of manufacture, and, in particular, to enable such a composition for a drug having low solubility in water.

BRIEF DESCRIPTION OF THE INVENTION

It has been found that a multi-granular controlled-release composition can be made by dissolving or dispersing the drug, along with a water-insoluble polymer, in a hot molten carrier, cooling the resultant material until it solidifies, and grinding the resultant solid into granules. The granules can then be filled into a hard gelatin capsule, or else mixed with other ingredients and made into tablets.

When the capsules or tablets disintegrate in gastrointestinal fluid, a multitude of granules is released from the capsules or tablets, and the drug is then gradually released from the granules.

In the case of a drug with low solubility in water, the carrier is preferably a substance in which the drug is readily soluble, so that when the drug is blended into the molten carrier, the drug is dissolved and is dispersed at molecular size.

If the carrier also is effective as a plastizer for the water-insoluble polymer, then when the polymer is added to the molten carrier, the carrier will plastizer the polymer and, upon cooling and solidification, cause the polymer to colasce into an insoluble matrix, from which the drug will be only slowly released in gastrointestinal fluid.

If the carrier does not act as a plastizer for the polymer, then a separate ingredient effective as a plastizer may also be incorporated into the molten mix.

DETAILED DESCRIPTION OF THE INVENTION

As aforesaid, a feature of the invention is that the drug and a water-insoluble polymer are mixed into a molten carrier. Suitable carriers will have a melting point between 35° C. and 200° C. The carrier will preferably be water-soluble, by which is meant having a solubility in water of at least 1 g per 100 g at 20° C., or at least readily dispersible in water.

Suitable carriers will include, for example, but are not limited to, sorbitol, mannitol, polyoxyl 40 hydrogenated castor oil, and polyethylene glycol having an average molecular weight of at least 1000.

Preferred as carrier is polyethylene glycol having an average molecular weight above 1000. Especially preferred is polyethylene glycol having an average molecular weight from about 3350 to about 8000. Hereinafter, polyethylene glycol having a particular average molecular weight will be referred to as "polyethylene glycol" followed by a number representing the appropriate average molecular weight. For example, "polyethylene glycol 8000" will be understood to mean polyethylene glycol having an average molecular weight of about 8000.

Suitable water-insoluble polymers will include any polymer that, upon dispersion in the molten carrier along with the drug and upon cooling and solidification, will form a water-insoluble matrix from which the drug will be released only slowly when granules of the matrix are immersed in gastrointestinal fluid. The term water-insoluble in reference to the polymer shall be understood to mean having a solubility in water of less than 0.1 percent by weight at 20° C.

Suitable polymers include but are not limited to ethylcellulose, and copolymers of acrylic and methacrylic acid and esters thereof. The polymer will preferably be used in the form of a fine powder to enable uniform dispersion.

Preferred polymers are copolymers of acrylic and methacrylic acid and esters thereof, such as those sold under the tradename Eudragit by Rohm Pharma GMBH. These polymers include, for example, the following:

i. The polymer sold as a powder under the tradename Eudragit SI 00, which complies with the specifications for Methacrylic Acid Copolymer Type B in the United States Pharmacopoeia and National Formulary.

ii. The polymer sold as a powder under the tradename Eudragit RLPO, which complies with the specifications for Ammonio Methacrylate Copolymer Type A in the United States Pharmacopoeia and National Formulary.

iii. The polymer sold as a powder under the tradename Eudragit RSPO, which complies with the specification for Ammonio Methacrylate Copolymer Type B in the United States Pharmacopoeia and National Formulary.

Especially preferred is a polymer complying with the specification for Ammonio Methyacrylate Copolymer Type B, such as Eudragit RSPO.

As aforesaid, when the drug and polymer are dispersed in the molten carrier and the carrier solidifies upon cooling, it is necessary that the polymer form a matrix from which the drug will be released only slowly in gastrointestinal fluid.

The formation of such a matrix is facilitated by including in the molten blend an ingredient that is an effective plastizer for the polymer. In the case of copolymers of acrylic and methacrylic acid and esters thereof, polyethylene glycol is an effective plastizer, so that when polyethylene glycol having molecular weight above 1000 is used as the carrier, no other plastizer is needed.

If the carrier and polymer are not selected such that the carrier is a plastizer for the polymer, another suitable plastizer may be included in the molten blend.

Compositions of the present invention may be made for a wide variety of drugs, regardless of solubility of the drug in water.

If the drug has low solubility in water, such as for example a substituted dihydropyridine such as nifedipine, it is advantageous to use as the carrier a substance in which the drug is a sufficiently soluble such that the drug can be fully dissolved in the molten carrier. For this purpose, it is desirable that the carrier be such that the drug has a solubility in the carrier of at least one percent by weight at the melting point of the carrier.

Nifedipine has good solubility in polyethylene glycols. Hence use of polyethylene glycol as carrier enables complete dissolving of nifedipine in the molten carrier, which eliminates the need to micronize the nifedipine.

As aforesaid, granules are made by melting the carrier, dispersing the drug and polymer therein (optionally along with other ingredients), cooling the mixture so that it solidifies, and grinding the resultant solid into granules. The other ingredients may include, for example, stearic acid as a lubricant to make it easier to remove the solidified material from the trays or other containers in which it is held while solidifying.

It is then necessary to process the granules into a dosage form suitable for oral administration.

This may be done for example, by filling the granules, optionally along with other ingredients, into 2-piece hard gelatin capsules.

Alternatively, the granules can be further processed into tablets. This is done by mixing the granules with other ingredients and compressing the mixture into tablets on a tablet press.

In the case of tablets, the other ingredients must be such that, when the tablet is immersed into gastrointestinal fluid, it will disintegrate to release the granules, so that thereafter the drug will be gradually released from the granules.

To make this happen, the other ingredients may include a disintegrant such as, for example, cellulose, starch, sodium starch glycolate or croscarmellose sodium, which will absorb water and swell so as to cause disintegration of the tablet. Alternatively, or in addition, the other ingredients may include a water-soluble material, such as, for example, lactose, mannitol, sorbitol, methylcellulose, or hydroxypropyl-methylcellulose (which is available in a variety of grades having various degress of hydroxypropyl substitution and various mean molecular weights), which will dissolve in gastrointestinal fluid thereby again causing the tablet to disintegrate and to release the granules.

The other ingredients may also include a lubricant such as, for example, magnesium stearate to avoid sticking to the tooling in the tabletting process.

The other ingredients may also include a glidant such as, for example, colloidal silicon dioxide, to improve flow in the tabletting process.

The final tablets may be uncoated or may have a film-coating applied to their surfaces using any of a number of polymer systems and processes well known in the art.

The production of compositions with the scope of the invention will be further illustrated by the following example, which is intended only to be illustrative and not limiting of the scope of the invention.

EXAMPLE

Tablets were made using ingredients in the following proportions:

| | | |
|---|---|---|
| Polyethylene Glycol 8000 | 97 | |
| Nifedipine | 33 | |
| Stearic Acid | 5 | |
| Eudragit RSPO | 25 | |
| Sorbitol | 89 | |
| Colloidal Silicon Dioxide | 1 | |
| | 250 | |

The polyethylene glycol 8000 was melted and further heated to a temperature of 120° C. The nifedipine was added and the mixture stirred until the nifedipine was fully dissolved. The stearic acid was then added and mixing was continued until the stearic acid melted and was dissolved in the mixture. The Eudragit RSPO was then added and mixing was continued until the Eudragit RSPO was well dispersed. The molten mixture was then poured into trays and allowed to solidify. The solid was then removed from the trays and ground into granules. The granules were then mixed with the sorbitol, and the resulting mixture was compressed into tablets of weight 250 mg per tablet.

Each tablet thus contained 33 mg of nifedipine.

A dissolution test was then done on the tablets using a type 2 dissolution apparatus as described in the Unites States Pharmacopoeia and National Formulary. The medium used was water containing 0.75% sodium lauryl sulfate, and the paddle speed was 100 rpm. It was found that the nifedipine in the tablets dissolved gradually over approximately 24 hours, which confirms that these tablets are suitable for use as a controlled release composition for once daily administration.

What is claimed:

1. A controlled-release composition comprising a multitude of granules, said granules comprising a carrier having a melting point between 35° C. and 200° C., within which there is dissolved or dispersed a drug and a water-insoluble polymer, wherein said composition is made by a process of heating said carrier to above its melting point, adding thereto said drug and said water-insoluble polymer, blending, cooling the resultant material until it solidifies, and grinding the resultant solid into granules, and wherein said composition is in the form of a tablet or capsule orally administerable to the gastrointestinal tract of a patient and wherein said tablet or capsule disintegrates in gastrointestinal fluid of said patient thereby releasing said multitude of granules into said fluid.

2. The composition as in claim 1 wherein either said carrier is an effective plastizer for said water-insoluble polymer or wherein the composition further comprises another ingredient which is an effective plasticizer for said water-insoluble polymer.

3. The composition as in claim 1 wherein the carrier has solubility in water of at least 1 g per 100 g at 20° C.

4. The composition as in claim 1, wherein the carrier is polyethylene glycol having an average molecular weight of at least 1000.

5. The composition as in claim 1 wherein said water-insoluble polymer is selected from ethylcellulose, and copolymers of acrylic and methacrylic acid and esters thereof.

6. The composition as in claim 5 wherein said water-insoluble polymer is an ammonio methyacrylate copolymer.

7. The composition as in claim 1 wherein said drug has a solubility of less than 0.1 per cent by weight in water at 20° C. and a solubility above one percent by weight in said carrier at the melting point of said carrier.

8. The composition as in claim 1 wherein said drug is a substituted dihydropyridine.

9. The composition as in claim 8 wherein the drug is nifedipine.

10. The composition as in claim 1 wherein said granules are mixed with one or more further excipients and formed into tablets which disintegrate in gastrointestinal fluid to release said granules.

* * * * *